(12) United States Patent
Bruno et al.

(10) Patent No.: US 10,130,426 B2
(45) Date of Patent: Nov. 20, 2018

(54) CUTTING HUMAN OR ANIMAL BONE TISSUE AND PLANNING SUCH CUTTING

(71) Applicant: ADVANCED OSTEOTOMY TOOLS AOT AG, Basel (CH)

(72) Inventors: Alfredo Bruno, Biel-Benken (CH); Mathias Griessen, Steffisburg (CH); Philippe Cattin, Windisch (CH)

(73) Assignee: Advanced Osteotomy Tools—AOT AG, Basel (CH)

( * ) Notice: Subject to any disclaimer, the term of this patent is extended or adjusted under 35 U.S.C. 154(b) by 102 days.

(21) Appl. No.: 14/900,862

(22) PCT Filed: Jun. 30, 2014

(86) PCT No.: PCT/EP2014/063793
§ 371 (c)(1),
(2) Date: Dec. 22, 2015

(87) PCT Pub. No.: WO2015/000823
PCT Pub. Date: Jan. 8, 2015

(65) Prior Publication Data
US 2016/0135890 A1    May 19, 2016

(30) Foreign Application Priority Data
Jul. 1, 2013    (EP) .................................... 13174509

(51) Int. Cl.
*A61B 18/20*    (2006.01)
*A61B 34/10*    (2016.01)
(Continued)

(52) U.S. Cl.
CPC ............ *A61B 18/203* (2013.01); *A61B 34/10* (2016.02); *A61B 18/201* (2013.01); *A61B 34/30* (2016.02);
(Continued)

(58) Field of Classification Search
CPC ................................ A61B 2018/00565; A61B 2018/00571–2018/0063; A61B 18/20–18/28; A61B 34/00–2034/108
(Continued)

(56) References Cited

U.S. PATENT DOCUMENTS 4,433,681 A    2/1984    Comparetto
4,728,330 A *  3/1988    Comparetto ....... A61B 17/1604
                                                                 433/177
(Continued)

FOREIGN PATENT DOCUMENTS

CN    202554079    11/2012

OTHER PUBLICATIONS

Written Opinion of the International Searching Authority issued in International Application No. PCT/EP2014/063793 dated Sep. 29, 2014.

*Primary Examiner* — Gary Jackson
*Assistant Examiner* — J. K. Jonathan Kuo
(74) *Attorney, Agent, or Firm* — Hoffmann & Baron, LLP

(57) ABSTRACT

Method for planning a process of cutting human or animal bone tissue. The method includes: obtaining initial data of an initial situation of the bone tissue; defining target data of a target situation of the bone tissue; and computing a cut geometry using the initial data and the target data for cutting the bone tissue apart. The cut geometry includes a structure such that the bone tissue is reassemblable at least in one degree of freedom in the target situation after being cut apart along the cut geometry. By shaping the structure of the cut geometry according to the target situation the planned cut can be provided with a particular function. Such a functional cut can geometrically define and restrict possible movements of cut apart bone portions. The functional cut can allow for comparably precisely repositioning the bone into
(Continued)

the target position and any movement therefrom can be prevented.

11 Claims, 7 Drawing Sheets

(51) Int. Cl.
  *A61B 34/30* (2016.01)
  *A61B 18/00* (2006.01)
  *A61B 34/20* (2016.01)
(52) U.S. Cl.
  CPC ............... *A61B 2018/00565* (2013.01); *A61B 2018/00601* (2013.01); *A61B 2018/20359* (2017.05); *A61B 2034/101* (2016.02); *A61B 2034/104* (2016.02); *A61B 2034/2055* (2016.02)
(58) Field of Classification Search
  USPC ..................................................... 606/79–85
  See application file for complete search history.

(56) References Cited

U.S. PATENT DOCUMENTS

| | | | |
|---|---|---|---|
| 6,485,495 B1 * | 11/2002 | Jenkinson | A61B 17/1604 606/167 |
| 2011/0082459 A1 * | 4/2011 | Aravot | A61B 17/1691 606/79 |
| 2012/0215227 A1 | 8/2012 | Fitzpatrick et al. | |

* cited by examiner

CUTTING HUMAN OR ANIMAL BONE TISSUE AND PLANNING SUCH CUTTING

CROSS-REFERENCE TO RELATED APPLICATIONS

This application is the U.S. National Phase of International Patent Application No. PCT/EP2014/063793, filed on 30 Jun. 2014, which claims benefit of European Patent Application No. 13174509.3, filed on 1 Jul. 2013, the contents of which are incorporated herein by reference in their entirety.

TECHNICAL FIELD

The present invention relates to a method for planning a process of cutting human or animal bone tissue, to a computer program for implementing such a method and to a process of cutting human or animal bone tissue. Such methods in which data of an initial situation of the bone tissue is obtained, a cut geometry is designed, the bone tissue is cut along the cut geometry and the bone tissue is reassembled after being cut apart can be used in many medical or surgical applications such as in reconstructive surgery.

BACKGROUND ART

In today's surgery it is often needed to separate human or animal bone tissue in plural pieces, to remove the single pieces from each other and to reassemble the pieces again. For example, in many applications in reconstructive surgery it is necessary to separate a bone in plural pieces and to reassemble the plural pieces in an adapted position for reshaping the bone to a target shape or situation. One example of such a reconstructive surgery application is correction of a patient's overbite. Thereby, in some cases the maxilla is divided in two or more pieces and reassembled in a target position. In the target position the two portions of the bone grow together during the healing process or are fixed together and the bone is reshaped accordingly. For separating or dividing the bone in such an application suitable cutting tools are used which allow applying a cut to the bone.

Or in other surgery applications it is necessary to temporarily divide a bone, e.g., in order to access a space covered by the bone. For example, in order to access the interior of the chest, e.g. in order to access the heart or lung, often the sternum is divided apart and reassembled after the intervention in the original position. Similarly, also for such dividing suitable bone cutting tools are used for separating the bone apart.

A problem occurring in today's surgery including separation of human or animal bone tissue is that conventional cutting tools usually have an insufficient precision such that reassembling the bone tissue causes adverse effects or an unsatisfying result. For example, conventional surgical saws produce a comparably wide cut and thereby remove comparably much bone substance. Also conventional cutting tools often cause collateral damages to the bone tissue near the cut which are to prevent if possible.

In this context, cutting tools have been developed which allow for an improved precise cutting of human and animal bone tissue. For example, WO 2011/035792 A1 describes a computer assisted and robot guided laser osteotome medical device. This device uses a robot arm guided laser, such as an Er:YAG laser, to cut human or animal bone tissue by photoablating the tissue along a predefined osteotomic line.

With such a device bone or other bone tissue can be cut with comparably high precision and comparably low collateral damages.

However, even though the mentioned modern cutting tools allow for improved applications in surgery, cutting bone tissue for reassembling it in a target position or shape can still be problematic. In particular, after being reassembled, the separated portions of the bone tissue can be at least comparably slightly shifted or moved in relation to each other such that the reassembled bone tissue is not precisely reshaped or rearranged in the target position. A possible way for preventing such shifting or moving can be to fix the separated portions of the bone tissue in the target position by external mechanical means such as screws, nails or the like. Such fixing can, however, be comparably cumbersome and laborious. Additionally, often the cut apart portions of the bone tissue are not suitably shaped in order to be properly reassembled in the target position such that auxiliary constructions have to be used.

Therefore, there is a need for cutting human or animal bone tissue in manner allowing reassembling cut apart portions of the bone tissue in a manner adapted to the intended application.

SUMMARY

According to the invention this need is settled by a method as it is defined by the features of independent claim 1, by a computer program as it is defined by the features of independent claim 6 and by a process as it is defined by the features of independent claim 7. Preferred embodiments are subject of the dependent claims.

In particular, the gist of the invention is the following: A method for planning a process of cutting human or animal bone tissue comprises: obtaining initial data of an initial situation of the bone tissue; defining target data of a target situation of the bone tissue; and computing a cut geometry using the initial data and the target data for cutting the bone tissue apart. Thereby, the cut geometry comprises a structure being shaped such that the bone tissue is reassemblable in an at least in one degree of freedom distinct manner in the target situation after being cut apart along the cut geometry.

The method according to the invention can completely or also partially be a computer implemented method. The term "bone tissue" in the context of the invention can relate to any human or animal bone or bone-like tissue. Particularly, it covers skeleton bones such as jaw bones, maxillas, sternums, skulls, cartilage and the like. The term "situation of the bone tissue" can relate to position and/or shape of the bone tissue. The initial situation of the bone tissue can be a bone tissue situation which has to be corrected or adapted. In such a case the initial situation of the bone tissue is different from the target situation of the bone tissue. The initial situation of the bone tissue can also be a situation which has to be temporarily changed, e.g. in order to open the interior of the body or the like. Thereby, the initial situation can be identical to the target situation. The terms "initial data" and "target data" can particularly relate to geometrical data defining the situation of the bone tissue. This geometrical data can be defined within a suitable coordinate system. The initial data can be obtained by measuring the bone tissue, e.g., by means of computer tomography (CT) or the like and providing measurement information, e.g., as digital data.

The term "degree of freedom" as used in connection with the invention relates to the movement of cut apart portions or pieces of the bone tissue in relation to each other. It can particularly relate to a rotational movement and/or a lateral movement in any possible direction. The term "distinct manner" in the context of the invention relates to an at least in one degree of freedom non-deviatable reassembling of the bone tissue in the target situation. In particular, it can relate to one or plural comparably precise target positions from which a continuous or stepless modification is excluded at least in the mentioned one degree of freedom. This means that in accordance with this term the bone tissue is reassemblable in any predefined target situation only and any continuous or floating deviation thereof in the at least one degree of freedom is not reasonably feasible. This can particularly differentiate the method according to the invention from any method in which bone tissue is cut apart and reassembled in a continuous manner along the cut, e.g., until an intended target situation is more or less achieved.

By shaping the structure of the cut geometry in accordance with the target situation of the bone the planned cut can be provided with a particular function. I.e., such a functional cut can geometrically define and restrict possible movements of cut apart bone portions in relation to each other. Thereby, the functional cut can allow for comparably precisely repositioning the bone into the target position and any movement therefrom at least in the one degree of freedom can be prevented. Also, such a functional cut allows for providing additional contact surface area compared to conventional cuts such that stronger connection can be achieved after reassembling and healing together.

Thus, the method according to the invention allows for cutting human or animal bone tissue whereas reassembling cut apart portions of the bone tissue in accordance with the intended application is already initially considered and implemented. Thereby, it is possible to assure that the bone tissue can be comparably precisely and stably reassembled in the target position without mandatorily requiring additional fixing means or the like. Inaccuracies of manual or similar positioning of the cut apart bone portions while reassembling can be minimized or even excluded.

Preferably, the structure of the cut geometry is shaped such that the bone tissue is reassemblable in all degrees of freedom distinct manner in the target situation after being cut apart along the cut geometry. The term "all degrees of freedom" relates in this context to a movement of the cut apart bone portions in relations to each other. This does particularly not include any movement for separating the cut apart bone portions from each other but only for positioning the cut apart bone portions in relation to each other. Like this, the target position can precisely be predefined by the geometry of the cut itself and any unintended movement of the cut apart bone portions in relation to each other can be prevented. Also tracking of the reassembling by external means can be prevented.

In one preferred embodiment, the structure of the cut geometry is shaped such that the bone tissue is reassemblable exclusively in one single target situation after being cut apart along the cut geometry.

In another preferred embodiment, the structure of the cut geometry is shaped such that the bone tissue is reassemblable in plural stepwise distinct target situations after being cut apart along the cut geometry. Thereby, the structure of the cut geometry preferably is computed using a periodic function and is periodically shaped in accordance with the periodic function. In this context, the term "periodic function" can relate to a complicated periodic function wherein complicated function can mean a function on top of a regular function such as a circular function or the like. The periodic function can particularly be a sinus or similar function, a triangular function or the like.

Preferably, the structure of the cut geometry comprises a convex curved portion and a concave curved portion corresponding to the convex curved portion wherein the convex curved portion is arranged in the concave curved portion when the bone tissue is in the target situation. With such a cut geometry a twist movement or rotation of the cut apart bone portions can be prevented whereas, in some embodiments, a rotational movement perpendicular to the cutting face can still be possible.

Preferably, the structure of the cut geometry comprises a convex wedged portion and a concave wedged portion corresponding to the convex wedged portion wherein the convex wedged portion is arranged in the concave wedged portion when the bone tissue is in the target situation. Thereby, the wedged portions can be defined by non-perpendicular surface angles on different sides of the wedged portion. With such a structure parallel displacement of the cut apart bone portions can be prevented.

Preferably, the structure of the cut geometry comprises a projection and a recess corresponding to the projection wherein the projection is arranged in the recess when the bone tissue is in the target situation. Thereby, the projection preferably comprises a bar and the recess a groove corresponding to the bar. Such an arrangement allows for blocking the cut apart bone portions in relation to each other whereas a parallel or lateral movement may still be possible. By providing a plurality of bars and corresponding grooves the distance between the bars can define a desired displacement distance.

Also, the projection preferably comprises a pin and the recess comprises a hole corresponding to the projection. Such a structure allows the cut to be provided with a plug like function. In particular, by arranging the pin inside the hole the cut apart portions of the bone tissue can be precisely plugged together in the target position.

A further aspect of the invention relates to a computer program comprising computer readable commands causing a computer to implement a method as described above when being loaded to or executed by the computer. Such a computer program allows for efficiently implementing the method according to the invention and its according effects.

Another further aspect of the invention relates to a process of cutting human or animal bone tissue. The process comprises: obtaining initial data of an initial situation of the bone tissue; defining target data of a target situation of the bone tissue; computing a cut geometry using the initial data and the target data for cutting the bone tissue apart, wherein the cut geometry comprises a structure being shaped such that the bone tissue is reassemblable in an at least in one degree of freedom distinct manner in the target situation after being cut apart along the cut geometry; cutting the cut geometry into the bone tissue; taking the bone tissue apart along the cut geometry; and reassembling the bone tissue in the target situation.

The process which can be an in vitro process implements the method according to the invention described hereinbefore. Accordingly, it also implements the effects and advantages of this method as described above. In consequence, the process according to the invention allows for cutting human or animal bone tissue whereas reassembling cut apart portions of the bone tissue in accordance with the intended application is already initially considered. Thereby, it is possible to assure that the bone tissue can be comparably precisely and stably reassembled in the target position without mandatorily requiring additional fixing means or the like. Inaccuracies of manual or similar positioning of the cut apart portions while reassembling can be minimized or even excluded.

Preferably, the cut geometry is cut into the bone tissue by a laser beam. Such a laser beam allows for precisely applying cuts in any angle and depth without substantially impairing the bone tissue or neighboring other tissue. Thereby, the laser beam preferably is provided by a laser source mounted to a robot arm. Such an arrangement allows for precisely moving and directing the laser beam in any degree of freedom such that comparably complicated cutting geometries can be applied. Thereby, the laser beam and the robot arm preferably are controlled by a computer, wherein the computer is arranged to compute the cut geometry using the initial data and the target data. In particular, the computer can use data previously obtained and determined from an algorithm which a-priori calculates the cutting path or geometry with the initial data to achieve the target geometry or position.

Preferably, by cutting the cut geometry into the bone tissue the bone tissue is cut in a first bone portion and a second bone portion wherein in the target situation the first bone portion and the second bone portion are displaced in relation to each other. In this way, the bone tissue can conveniently be reshaped which is necessary in many surgical applications.

These and other aspects of the invention will be apparent from and elucidated with reference to the embodiment(s) described hereinafter.

BRIEF DESCRIPTION OF THE DRAWINGS

In the following, the method according to the invention, the computer program according to the invention and the process according to the invention are described in more detail by way of exemplary embodiments and with reference to the attached drawings, in which.

DETAILED DESCRIPTION

In the following description certain terms are used for reasons of convenience and are not to be interpreted as limiting. The terms "right", "left", "up", "down", "horizontal", "vertical", "upper", "lower", "under" and "above" refer to directions in the figures. The terminology comprises the explicitly mentioned terms as well as their derivations and terms with a similar meaning.

Figure 1:
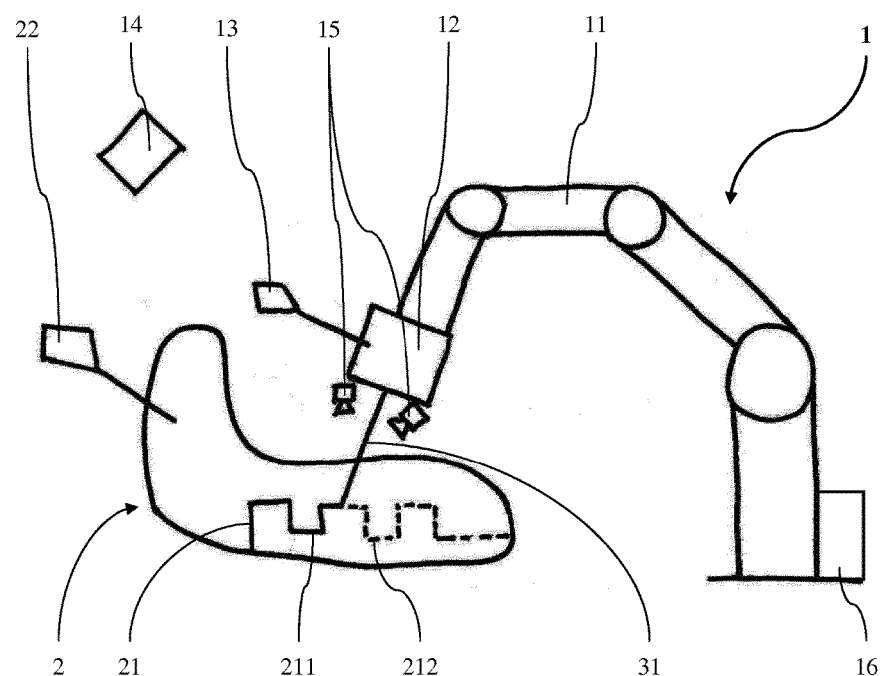
FIG. 1 shows a computer assisted surgery apparatus for implementing an embodiment of a method, computer program and process in accordance with the invention.

FIG. 1 shows a schematic view of a computer assisted surgery apparatus 1 comprising an embodiment of a computer program according to the invention and being arranged for applying the method according to the invention and the process according to the invention. The apparatus 1 comprises a robot arm 11 being fixedly arranged at its one longitudinal end on a support platform. On the other longitudinal end of the robot arm a laser head 12 is arranged which is movable by the robot arm 11 in all degrees of freedom. The laser head 12 has a laser source, a focusing optics and adjustable mirrors for redirecting the laser. Fixedly mounted to the laser head 12 is a monitoring system of the laser head 12 having two cameras 15. Furthermore, a marker shield 13 is attached to the laser head 12. The apparatus 1 also comprises a tracking device 14 and a control unit having a computer 16 running the computer program.

In the sphere of action of the apparatus 1 a mandibula 2 or lower jaw as bone tissue is arranged. A marker shield 22 is attached to the mandibula. The laser head 12 of the apparatus provides a laser beam 31 onto the mandibula 2 along an osteotomic line 21 defining a cut geometry. Thereby, the mandibula 2 is cut by the laser beam 31 along the osteotomic line 21. The osteotomic line has a realized portion 211, i.e. the cut, in which the mandibula 2 is cut by the laser beam 31 already and a planned portion 212 in which the mandibula 2 still is to cut. The osteotomic line 21 has a periodic rectangular shape with right angles such that plural parallel bars and grooves are formed in the mandibula 2.

In use of the apparatus 1, initial geometrical data of the mandibula 2 is obtained, e.g. by means of computer tomography (CT), three-dimensional stereo reconstruction using the two cameras 15, using one camera and a scanned laser beam for three-dimensional reconstruction or optical coherence tomography (OCT). The initial geometrical data is processed by the computer 16 wherein target geometrical data of a target situation of the mandibula 2 is a-priori defined by means of the computer 16. The computer 16 then models and calculates an ideal or suitable cut geometry, i.e., in FIG. 1, the osteotomic line 21. Thereby, the osteotomic line 21 structures the cut geometry such that the mandibula 2 can be divided apart and reassembled in a horizontally distinct manner by creating the bars and grooves.

The mandibula 2 is then arranged at a suitable location in the sphere of action of the apparatus 1 and the laser beam 31 provided by the laser head 12 cuts the mandibula 2 along the osteotomic line 21. For that purpose the laser head 12 is moved by the robot arm 11 and the laser beam 31 is adjusted by the mirrors of the laser head 12. In particular, the position and orientation of the laser beam 31 is automatically controlled by the control unit such that the mandibula 2 is precisely cut along the osteotomic line 21.

After being cut the mandibula 2 is taken apart by vertically moving the lower portion from the upper portion of the mandibula 2. The lower portion is then shifted by an appropriate number of bars and reassembled by arranging bars in grooves other than the grooves they originate from. Thereby, the lower portion can be horizontally and distinctly or stepwise displaced to the right by a suitable number of bars such that the mandibula 2 is in the target situation.

The following applies to the rest of this description. If, in order to clarify the drawings, a figure contains reference signs which are not explained in the directly associated part of the description, then it is referred to previous description sections.

In the following, examples of cut geometries for cutting bone tissue apart and examples of applications of such cut geometries or functional cuts are explained in more detail. These cut geometries which can be generated in a method or a process according to the invention particularly comprise a structure which is shaped to allow reassembling the bone tissue in an at least in one degree of freedom distinct manner after being cut apart along the cut geometry.

Figure 2:
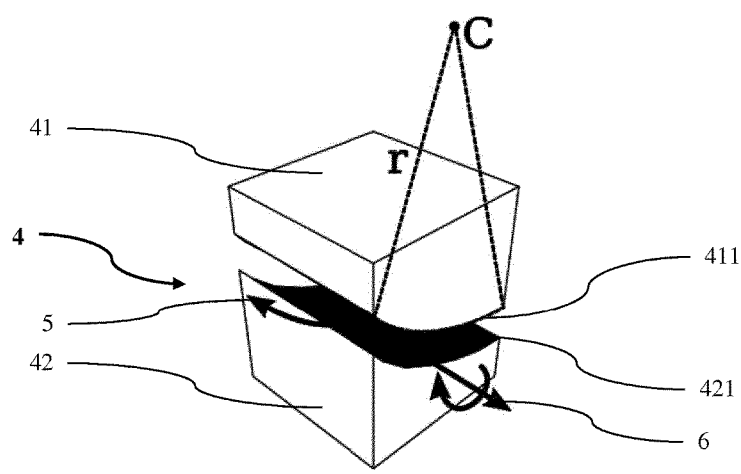
FIG. 2 shows a curvature cut based on a cut geometry having a structure with a convex curved portion and a concave curved portion provided by a method and process according to the invention.

FIG. 2 shows a schematic view of a bone tissue 4 which is cut apart along a cut geometry having a curvature shaped structure into an upper first bone portion 41 and a lower second bone portion 42. In particular, the structure has a convex curved portion 411 at the first bone portion 41 and a corresponding concave curved portion 421 at the second bone portion 42.

The curvature shaped structure of the bone tissue 4 is defined by a center C and a radius r of the curvature cut creating the convex curved portion 411 and the concave shaped portion 421. Whereas the first bone portion 41 and the second bone portion 42 can be moved in a tangential direction 5 allowing a rotation perpendicular to a cutting line and in a lateral direction 6 in relation to each other, other degrees of freedom such as twisting or the like are avoided by the cut geometry. Thus, the cut geometry only allows a distinct reassembling of the first bone portion 41 and the second bone portion 42.

Figure 3:
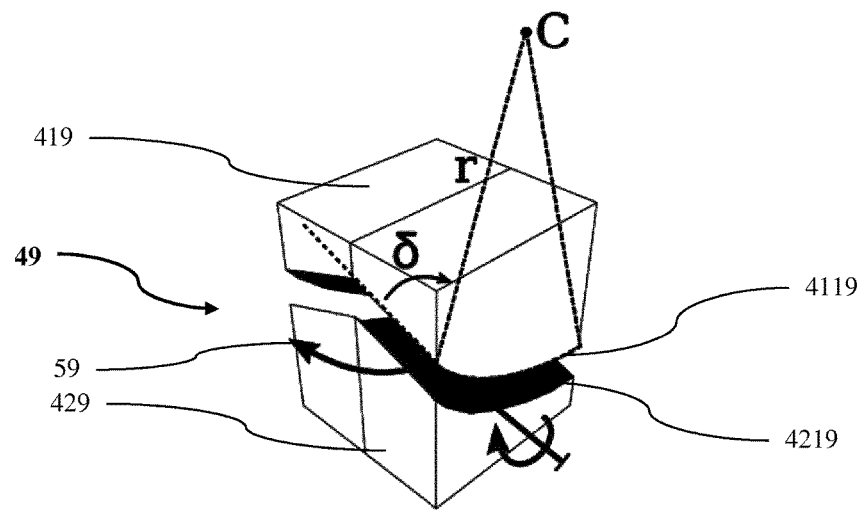
FIG. 3 shows a wedged cut based on a cut geometry having a structure with a convex wedged portion and a concave wedged portion provided by a method and process according to the invention.

In FIG. 3 a schematic view of a bone tissue 49 which is cut apart along a cut geometry having a wedged shaped structure in an upper first bone portion 419 and a lower second bone portion 429. In particular, the structure has a convex wedged portion 4119 at the first bone portion 419 and a corresponding concave wedged portion 4219 at the second bone portion 429.

The wedged shaped structure of the bone tissue 49 is defined by a center C and a radius r, wherein the radius r changes in a lateral direction such that a non-perpendicular angle δ is formed laterally between the surface of the convex wedged portion 4119 and the radius r. By doing cuts with such non-perpendicular cutting angle from both sides the wedged surfaces of the convex wedged portion 4119 and the corresponding concave wedged portion 4219 can be achieved which prevents from parallel or lateral displacement but still allows the first bone portion 419 and the second bone portion 429 to be moved in a tangential direction 59. Thus, the cut geometry only allows a distinct reassembling of the first bone portion 419 and the second bone portion 429.

Figure 4:
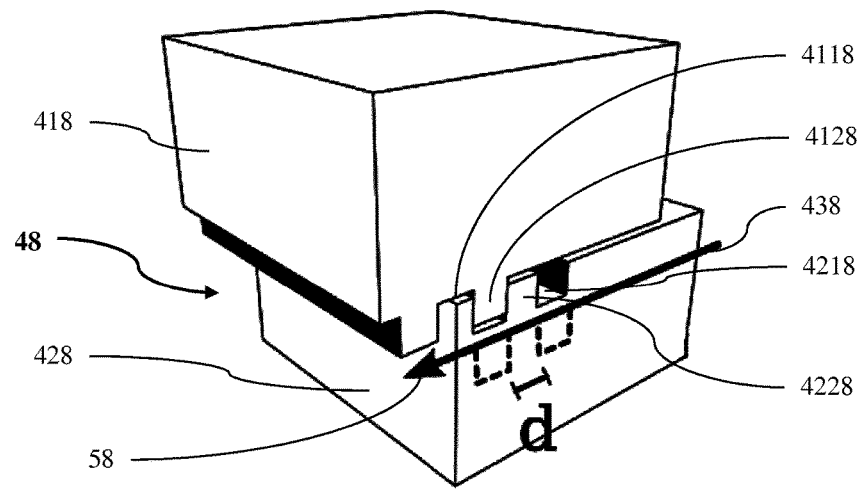
FIG. 4 shows a plug cut based on a cut geometry having a structure with bars and grooves provided by a method and process according to the invention.

FIG. 4 shows a schematic view of a bone tissue 48 which is cut apart along a cut geometry having a structure with plural bars 4128, 4228 and plural grooves 4118, 4218 into an upper first bone portion 418 and a lower second bone portion 428. In particular, the structure has two bars 4128 separated from each other by a groove 4118 at the first bone portion 418 and two corresponding grooves 4218 separated by a bar 4228 at the second bone portion 428. Thereby, the bars 4128 of the first bone portion 418 are projecting downwardly into the direction of the second bone portion 428 and the bar 4228 of the second bone portion 428 is projecting upwardly into the direction of the first bone portion 418. The bars 4128, 4228 and the grooves 4118, 4218 have an equal width, i.e. distance d.

As shown in FIG. 4 the bone tissue 48 is reassembled after being taken apart such that one of the bars 4128 of the first bone portion 418 is arranged in one of the grooves 4218 of the second bone portion 428 neighbouring the groove 4218 it is originating from. In particular, the right-hand bar 4128 of the first bone portion 418 which originally was associated to the right-hand groove 4218 of the second bone portion 428 is arranged in the left-hand groove 4218 of the second bone portion 428. Like this, the first bone portion 418 is shifted in relation to the second bone portion 428 in a longitudinal direction 58 by the distance 2*d. Thereby, the distance 2*d defines the desired displacement distance such that longitudinal shifting of the first bone portion 418 in relation to the second portion 428 is exactly predefined and a deviation thereof can be prevented. Thus, the cut geometry only allows a distinct reassembling of the first bone portion 418 and the second bone portion 428 into a predefined target position. Tracking the shifting movement with an external tracking system and manually tuning the shifting is not necessary.

Figure 5:
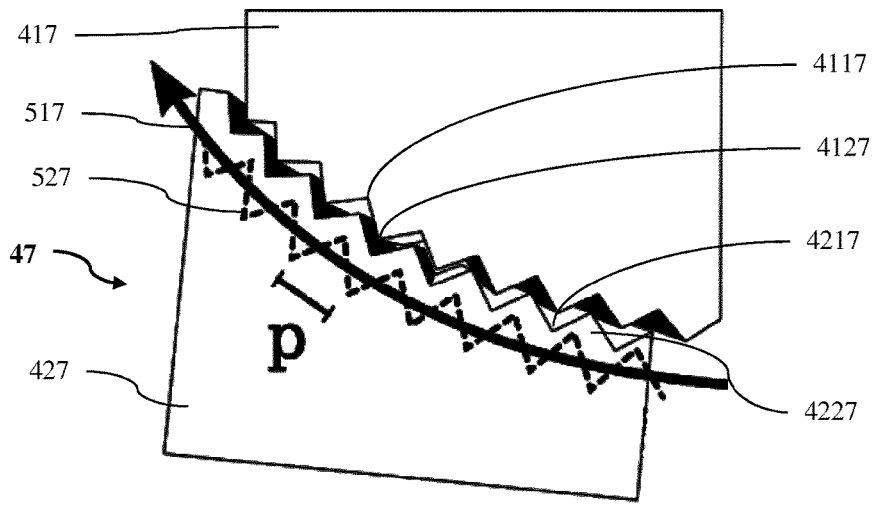
FIG. 5 shows a periodic cut based on a cut geometry having a periodic shape overlaying a curved cutting line provided by a method and process according to the invention.

In FIG. 5 a schematic view of a bone tissue 47 which is cut apart along a cut geometry having a periodic shaped structure into an upper first bone portion 417 and a lower second bone portion 427 is shown. In particular, in the structure of the cut geometry a base cutting line 517 is overlaid with a periodic triangular function 527 such that the first bone portion 417 is provided with series of triangular projections 4127 and triangular recesses 4117 having a period p and the second bone portion 427 is provided with corresponding series of triangular projections 4227 and triangular recesses 4217 having the period p. Thereby, a displacement distance is defined in steps corresponding to the period p.

As shown in FIG. 5 the bone tissue 47 is reassembled after being taken apart such that the triangular projections 4127 of the first bone portion 417 are arranged in triangular recesses 4217 of the second bone portion 427 neighbouring the recesses 4217 they originate from. Thereby, the second bone portion 427 is shifted along the base cutting line 517 by the period p. The period p defines the desired displacement step distance such that longitudinal shifting of the first bone portion 417 in relation to the second portion 427 is exactly predefined and a deviation from the predefined steps can be prevented. Thus, the cut geometry only allows a distinct reassembling of the first bone portion 417 and the second bone portion 427 into a predefined target position. Tracking the shifting movement with an external tracking system and manually tuning the shifting is not necessary.

In an embodiment not explicitly shown in the Figs. the periodic shaped structure shown in FIG. 5 is combined with the wedged shaped structure of FIG. 3.

Figure 6:
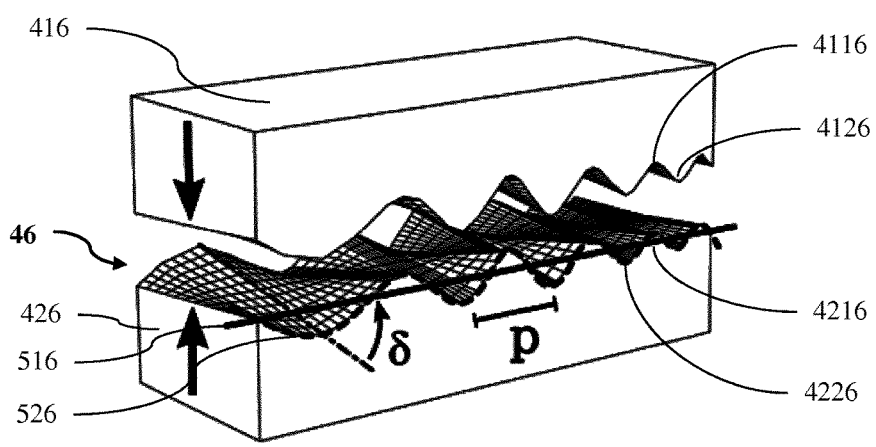
FIG. 6 shows a complicated periodic cut based on a cut geometry having a complicated periodic shape overlaying a straight cutting line provided by a method and process according to the invention.

FIG. 6 shows a schematic view of a bone tissue 46 which is cut apart along a cut geometry having a complicated shaped structure into an upper first bone portion 416 and a lower second bone portion 426. In particular, in the structure of the cut geometry a base cutting line 516 is overlaid with a sinusoidal function 526 with a non-uniform period p generating plural non-uniform projections 4126 and recesses 4116 at the first bone portion 416 and corresponding plural non-uniform projections 4216 and recesses 4216 at the second bone portion 426. In addition thereto, the sinusoidal function 526 varies in a lateral direction of the bone tissue 46 such that a non-perpendicular lateral cutting angle δ is formed.

By changing the cutting angle δ with varying sinusoidal functions, a twisted cutting surface is achieved. This prevents from parallel or lateral displacement as well as from longitudinal displacement. While using the non-uniform period p and the changing cutting angle δ, the first bone portion 416 and the second bone portion 426 only match at one single position along the cutting line 516. Thus, such slanted cutting surface and non-period cutting function combined results in two bone portions 416, 426 which only match together at the original position of the initial situation. Thus, the cut geometry only allows a distinct reassembling of the first bone portion 416 and the second bone portion 426 into a predefined target position which is equal to the initial position.

Figure 7:
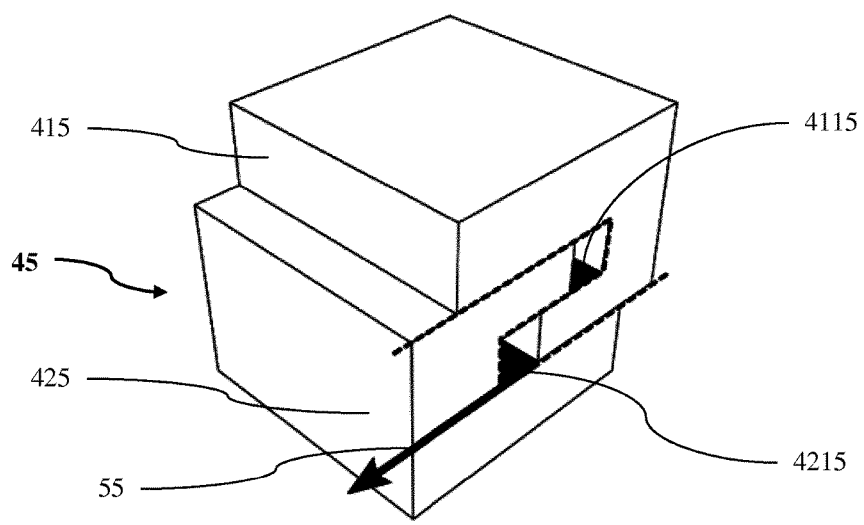
FIG. 7 shows a discontinuous cut provided by a method and process according to the invention.

In FIG. 7 a schematic view of a bone tissue 45 which is cut apart along a cut geometry having a discontinuously shaped structure into an upper first bone portion 415 and a lower second bone portion 425 is shown. In particular, in the structure of the cut geometry the first bone portion 415 comprises a first hook member 4115 and the second bone portion a second hook member 4215. The first hook member 4115 engages into the second hook member 4215 such that first bone portion 415 is movable in relation to the second bone portion mainly in a shifting direction 55 only.

As shown in FIG. 7 the second bone portion 425 is displaced in relation to the first bone portion 415 along the shifting direction 55 such that cavities are formed between the first bone portion 415 and the second bone portion 425. Like this, the comparably complicated discontinuous structure allows for combinations with plates and/or spacers to create a target position where the first bone portion 415 is only partially connected to the second bone portion 425.

Figure 8:
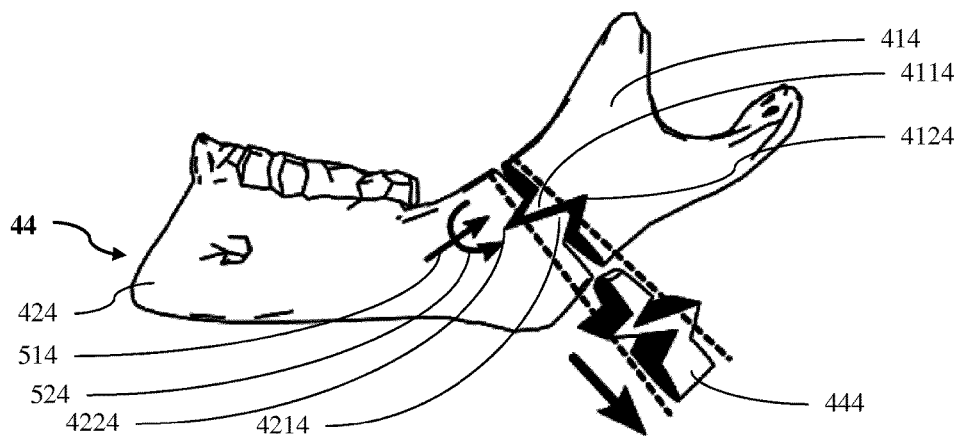
FIG. 8 shows a removing cut provided by a method and process according to the invention.

FIG. 8 shows a schematic view of a mandibula 44 which is cut apart along a cut geometry into an right-hand first mandibula portion 414 and a left-hand second mandibula portion 424 wherein the cut geometry is structured to remove a mandibula piece 444. In particular, the structure of the cut geometry comprises a first triangular projection 4114 and a first triangular recess 4124 arranged at the first mandibula portion 414 and a corresponding second triangular projection 4214 and a second triangular recess 4224 arranged at the second mandibula portion 424.

As shown in FIG. 8 when being reassembled the mandibula piece 444 is removed. Furthermore, the structure of the cut geometry is shaped such that the second mandibula piece is displaced in a displacement direction 514 and rotated in a pivot direction 524 when the first projection 4114 is arranged in the second recess 4224 and the second projection 4214 is arranged in the first recess 4124. Thus, the cut geometry only allows a distinct reassembling of the first mandibula portion 414 and the second mandibula portion 424 into a predefined target position in which the first mandibula portion 414 is shifted and rotated in relation to the second mandibula portion 424. Thus, the cut geometry only allows a distinct reassembling of the first bone portion 416 and the second bone portion 426 into a predefined target position.

Like this, dependent on the application, cuts can be provided where a certain part or piece is removed. For example, in orthognathic surgery an overbite can be corrected by removing a part from the mandibula as shown in FIG. 8. Doing this with a designed removal cut, the displacement and rotation of the mandibula 44 can be exactly defined.

Figure 9:
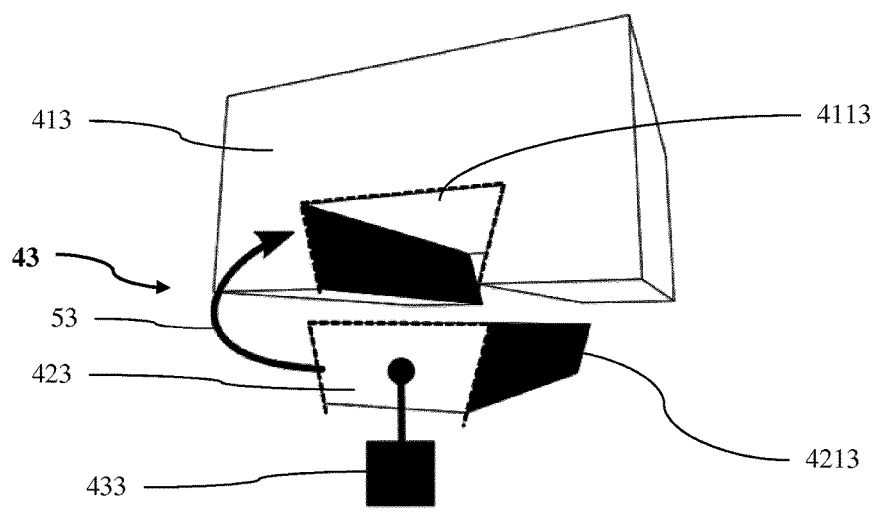
FIG. 9 shows a replacing cut provided by a method and process according to the invention.

In FIG. 9 a schematic view of a bone tissue 43 cut apart along a cut geometry structured for a replacement into an upper first bone portion 413 and a lower second bone portion 423 is shown. In particular, the structure of the cut geometry has a trapezoid recess 4113 in the first bone portion 413 and the second bone portion 423 has a corresponding trapezoid body 4213. Like this, the second bone portion 423 can only be connected to the first bone portion 413 by shifting it into a connection direction 53. In the reassembled bone tissue 43 the second bone portion 423 is held in the first bone portion 413 such that it cannot be displaced downwardly therefrom such as, e.g., by a weight 433.

Such a cut geometry does also allow for a transplantation of bone or similar tissue. Thereby, the second bone portion 423 is not reassembled to the first bone portion 413 it is originating from but to a different first bone portion of a target bone tissue. Such an application could, e.g., be a ligament replacement in the knee.

Figure 10:
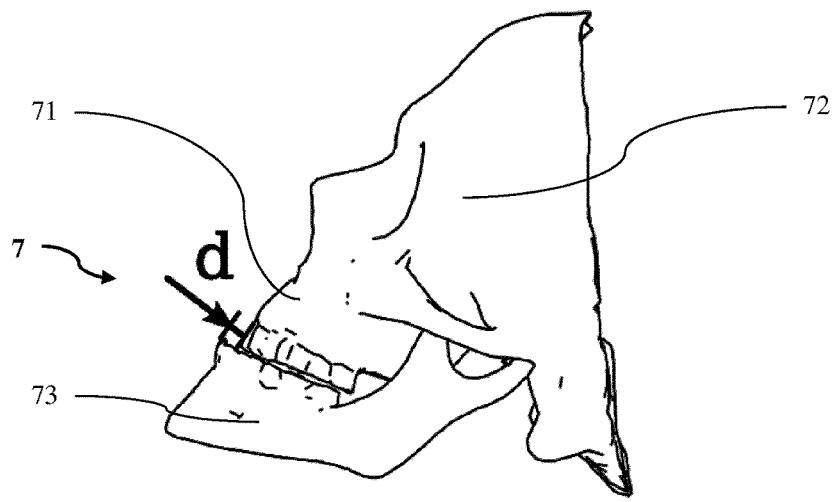
FIG. 10 shows an initial situation of an example of maxillary orthognathic surgery applying a method and process in accordance with the invention.

FIG. 10 shows a schematic view of a skull 7 in an initial situation of an example of a maxillary orthognathic process. The skull 7 comprises a cranium 72 with a maxilla 71 and a mandibula 73. The mandibula 73 projects above the maxilla 71 in a distal direction by displacement d such that an overbite is formed. To correct the overbite the maxilla 71 has to be cut and displaced.

Figure 11:
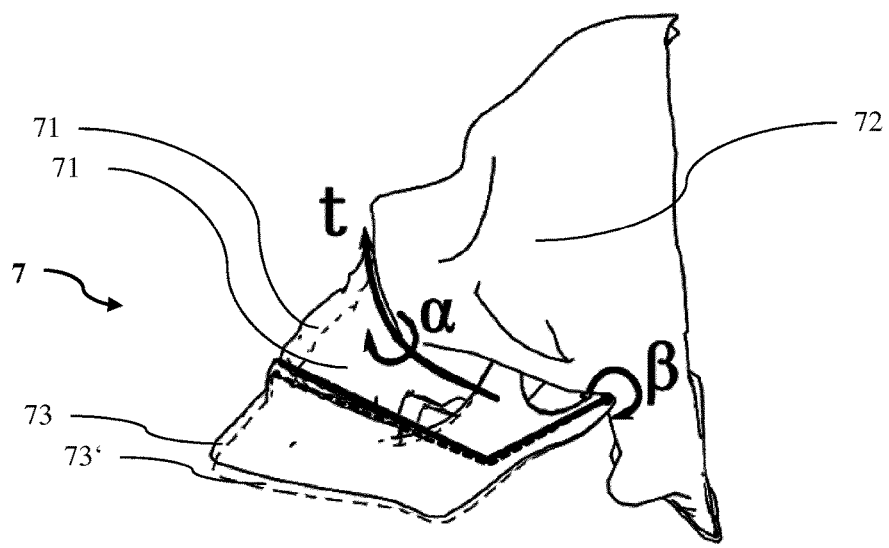
FIG. 11 shows a target situation of the example of FIG. 10.

In FIG. 11 the skull 7 is shown in a target situation wherein for allowing a comparison the initial situation of the skull 7 is indicated in dotted lines. The reference signs related the initial situation are the same as the reference signs related to the target situation provided with an apostrophe. This cut for correcting the overbite is done from the concha nasalis toward the pterygoideus. As the corresponding cutting line t is not parallel to the displacement d of the bite, shifting along this cutting line t does also lift the maxilla 71. To get a suitable match of maxilla 71 and mandibula 73 in the target situation the curvature of the cutting line t is chosen such that a rotation α of the maxilla 71 and a rotation β of the mandibula 73 are essentially the same.

Figure 12:
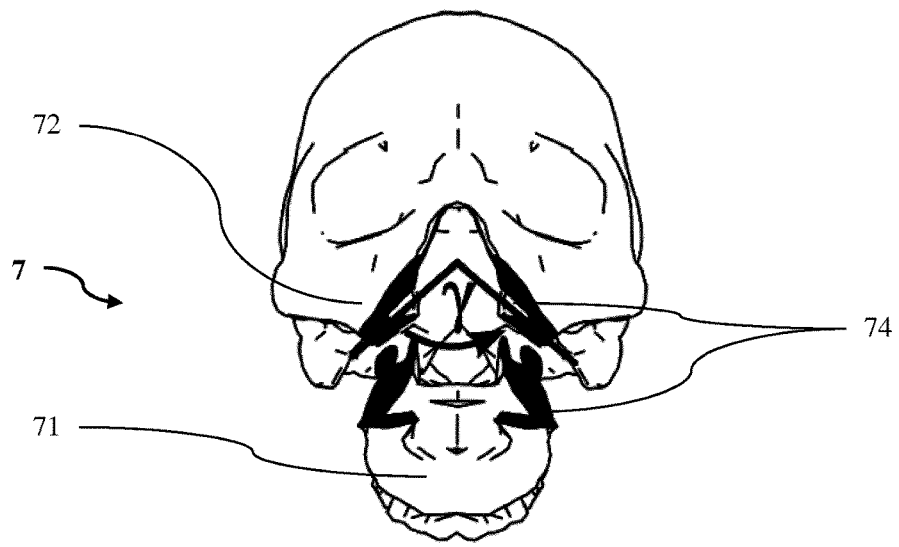
FIG. 12 shows cutting geometries of the example of FIG. 10.

As shown in FIG. 12 this is done with a wedged cutting surface γ guiding the displacement d into the desired direction and also preventing from cutting the palatina.

Figure 13:
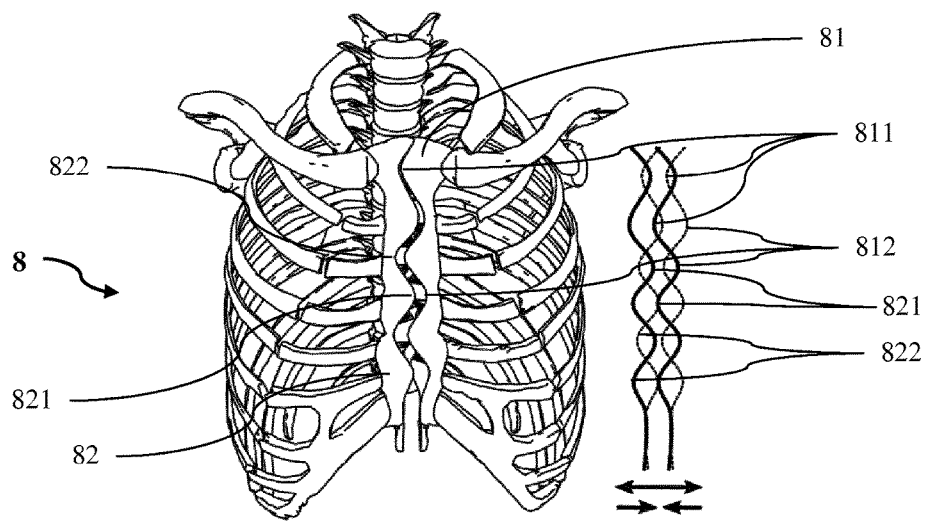
FIG. 13 shows an example of sternum opening surgery applying a method and process in accordance with the invention.

FIG. 13 shows an example of a sternum opening surgery process. A sternum 8 is cut along a cut geometry with a twisted structure into a right-hand first sternum portion 81 and a left-hand second sternum portion 82. The structure of the cut geometry is defined by a periodic sinus function with a non-uniform period generating plural non-uniform projections 811 and recesses 812 at the first sternum portion 81 and corresponding plural non-uniform projections 821 and recesses 822 at the second sternum portion 82. In addition thereto, the sinusoidal function varies in a proximal or interior direction of the sternum 8 such that a non-perpendicular respective cutting angle is formed. Using such a non-periodic cutting function and a twisted cutting surface for opening the sternum 8 can guarantee that the chest is closed again at the original position. Thus, the cut geometry only allows a distinct reassembling of the first sternum portion 81 and the second sternum portion 82 into a predefined target situation which is equal to the initial situation.

Figure 14:
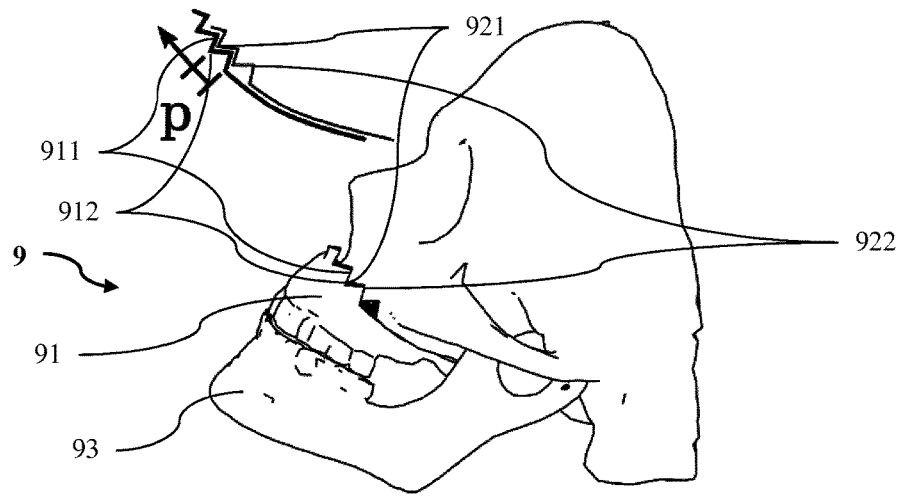
FIG. 14 shows an example of maxilla displacement surgery applying a method and process in accordance with the invention.

In FIG. 14 a schematic view of a skull 9 in a target situation of another example of maxilla displacement surgery is shown. Thereby, the skull 9 comprises a cranium 92 with a maxilla 91 and a mandibula 93. The mandibula 93 which originally projected above the maxilla 91 in a distal direction is corrected by cutting the maxilla 91 from the cranium 92 along a cut geometry and reassembling it in the target situation. The cut geometry comprises a structure with a periodic triangular function with period p such that plural triangular projections 911 and plural triangular recesses 912 are formed at the maxilla 91 and corresponding plural triangular projections 921 and plural triangular recesses 922 are formed at the cranium 92.

The maxilla 91 is advanced in relation to the cranium 92 by one period p such that the projections 911 of the maxilla 91 are arranged in the recesses 922 of the cranium 92 distally neighbouring the recesses 922 they originate from. Like this, it is possible to make sure that the cut maxilla 91 is displaced exactly by the target distance, i.e. the period p.

While the invention has been illustrated and described in detail in the drawings and foregoing description, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below.

The invention also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims ort the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Any reference signs in the claims should not be construed as limiting the scope.

A computer program may be stored/distributed on a suitable medium, such as an optical storage medium or a solid-state medium supplied together with or as part of other hardware, but may also be distributed in other forms, such as via the Internet or other wired or wireless telecommunication systems. In particular, e.g., a computer program can be a computer program product stored on a computer readable medium which computer program product can have computer executable program code adapted to be executed to implement a specific method such as the method according to the invention. Furthermore, a computer program can also be a data structure product or a signal for embodying a specific method such as the method according to the invention.

The invention claimed is:

1. A computer implemented method for planning a process of cutting human or animal bone tissue, the method comprising;
    obtaining, via a computing device, initial data of an initial situation of the bone tissue;
    defining, via the computing device, target data of a target situation of the bone tissue; and
    computing, via the computing device, a cut geometry using the initial data and the target data for cutting the bone tissue apart,
    wherein the cut geometry is a structure comprising a convex wedged portion and a concave wedged portion that corresponds to the convex wedged portion, the structure being shaped so that the bone tissue is capable of separation and reassembly at least in one degree of freedom distinct manner in the target situation after being cut apart according to the cut geometry, and
    wherein the convex wedged portion is arranged in the concave wedged portion when the bone tissue is reassembled in the target situation so that the structure allows tangential displacement but prevents parallel or lateral displacement of the convex wedged portion in relation to the concave wedged portion.

2. The method according to claim 1, wherein the structure of the cut geometry is shaped such that the bone tissue is capable of reassembly in all degrees of freedom distinct manner in the target situation after being cut apart according to the structure of the cut geometry.

3. The method according to claim 1, wherein the structure of the cut geometry is shaped such that the bone tissue is capable of reassembly exclusively in one single target situation after being cut apart according to the structure of the cut geometry.

4. The method according to claim 1, wherein the structure of the cut geometry is shaped such that the bone tissue is capable of reassembly in plural stepwise distinct target situations after being cut apart according to the structure of the cut geometry.

5. The method according to claim 4, wherein the structure of the cut geometry is computed using a periodic function and periodically shaped in accordance with the periodic function.

6. A computer readable medium comprising computer readable commands that, when executed by a computer, cause the computer to perform operations for planning a process of cutting human or animal bone tissue, the operations comprising:
    obtaining initial data of an initial situation of the bone tissue;
    defining target data of a target situation of the bone tissue; and
    computing a cut geometry using the initial data and the target data for cutting the bone tissue apart,
    wherein the cut geometry is a structure comprising a convex wedged portion and a concave wedged portion that corresponds to the convex wedged portion, the structure being shaped so that the bone tissue is capable of separation and reassembly at least in one degree of freedom distinct manner in the target situation after being cut apart according to the cut geometry, and wherein the convex wedged portion is arranged in the concave wedged portion when the bone tissue is reassembled in the target situation so that the structure allows tangential displacement but prevents parallel or lateral displacement of the convex wedged portion in relation to the concave wedged portion.

7. A process of cutting human or animal bone tissue, the process comprising obtaining initial data of an initial situation of the bone tissue;

defining target data of a target situation of the bone tissue;

computing a cut geometry using the initial data and the target data for cutting the bone tissue apart, wherein the cut geometry is a structure comprising a convex wedged portion and a concave wedged portion that corresponds to the convex wedged portion, the structure being shaped so that the bone tissue is capable of separation and reassembly at least in one degree of freedom distinct manner in the target situation after being cut apart according to the cut geometry;

cutting the bone tissue according to the cut geometry;

separating the bone tissue into the convex wedged portion and the concave wedged portion; and reassembling the convex wedged portion and the concave wedged portion in the target situation so that the structure allows tangential displacement but prevents parallel or lateral displacement of the convex wedged portion in relation to the concave wedged portion.

8. The process according to claim 7, wherein a laser beam is used to cut bone tissue according to the cut geometry.

9. The process according to claim 8, wherein the laser beam is provided by a laser source mounted to a robot arm.

10. The process according to claim 9, wherein the laser beam and the robot arm are controlled by a computer, wherein the computer is arranged to compute the cut geometry using the initial data and the target data.

11. The process according to claim 7, wherein in the target situation the convex wedged portion and the concave wedged portion are displaced in relation to each other.

* * * * *